US010525035B2

(12) United States Patent
Muller et al.

(10) Patent No.: US 10,525,035 B2
(45) Date of Patent: Jan. 7, 2020

(54) METHODS AND COMPOSITIONS FOR THE TREATMENT OF RETINOPATHY AND OTHER OCULAR DISEASES

(71) Applicant: LANKENAU INSTITUTE FOR MEDICAL RESEARCH, Wynnewood, PA (US)

(72) Inventors: Alexander J. Muller, Swarthmore, PA (US); Arturo Bravo-Nuevo, Medford, MA (US); Arpita Mondal, Philadelphia, PA (US); Courtney Smith, Springfield, PA (US); Hollie E. Flick, Philadelphia, PA (US)

(73) Assignee: LANKENAU INSTITUTE FOR MEDICAL RESEARCH, Wynnewood, PA (US)

( * ) Notice: Subject to any disclaimer, the term of this patent is extended or adjusted under 35 U.S.C. 154(b) by 0 days.

(21) Appl. No.: 15/533,201

(22) PCT Filed: Dec. 18, 2015

(86) PCT No.: PCT/US2015/066737
§ 371 (c)(1),
(2) Date: Jun. 5, 2017

(87) PCT Pub. No.: WO2016/100851
PCT Pub. Date: Jun. 23, 2016

(65) Prior Publication Data
US 2017/0360751 A1 Dec. 21, 2017

Related U.S. Application Data

(60) Provisional application No. 62/093,848, filed on Dec. 18, 2014.

(51) Int. Cl.
| | |
|---|---|
| A61K 31/4245 | (2006.01) |
| A61K 31/41 | (2006.01) |
| A61K 31/405 | (2006.01) |
| A61K 9/00 | (2006.01) |
| C12N 15/113 | (2010.01) |

(52) U.S. Cl.
CPC .......... *A61K 31/405* (2013.01); *A61K 9/0048* (2013.01); *C12N 15/1136* (2013.01); *C12N 2310/14* (2013.01)

(58) Field of Classification Search
CPC ... A61K 31/4245; A61K 31/41; A61K 31/405
See application file for complete search history.

(56) References Cited

U.S. PATENT DOCUMENTS

| | | | |
|---|---|---|---|
| 7,705,022 B2 | 4/2010 | Prendergast et al. | |
| 7,714,139 B2 | 5/2010 | Prendergast et al. | |
| 8,008,281 B2 | 8/2011 | Prendergast et al. | |
| 2006/0258719 A1 | 11/2006 | Combs et al. | |
| 2008/0119491 A1 | 5/2008 | Combs et al. | |
| 2008/0146624 A1 | 6/2008 | Combs et al. | |
| 2008/0182882 A1 | 7/2008 | Combs et al. | |
| 2008/0214546 A1 | 9/2008 | Combs et al. | |
| 2009/0253706 A1 | 10/2009 | Muller et al. | |
| 2013/0177590 A1 | 7/2013 | Combs et al. | |
| 2014/0011889 A1 | 1/2014 | Sardi | |
| 2014/0023663 A1 | 1/2014 | Combs et al. | |
| 2014/0066625 A1 | 3/2014 | Mautino et al. | |
| 2014/0161720 A1 | 6/2014 | Garkavtsev et al. | |
| 2016/0015805 A1* | 1/2016 | Azab ................. | A61K 39/3955 424/142.1 |

FOREIGN PATENT DOCUMENTS

| | | |
|---|---|---|
| WO | 2004/093871 A1 | 11/2004 |
| WO | 2004/094409 A1 | 11/2004 |
| WO | 2007/050963 A1 | 5/2007 |
| WO | 2008/115804 A1 | 9/2008 |
| WO | 2009/073620 A1 | 6/2009 |
| WO | 2009/132238 A1 | 10/2009 |
| WO | 2011/056652 A1 | 5/2011 |
| WO | 2012/142237 A1 | 10/2012 |
| WO | 2013/173635 A1 | 11/2013 |
| WO | 2014/078655 A1 | 5/2014 |
| WO | 2014/134355 A1 | 9/2014 |
| WO | 2014/159248 A1 | 10/2014 |

OTHER PUBLICATIONS

Park et al. Ocular Immunology and Inflammation, 2010, vol. 18, Issue 1, Abstract.*
Ishida, S., et al., "VEGF164-mediated Inflammation Is Required for Pathological, but Not Physiological, Ischemia-induced Retinal Neovascularization" J. Exp. Med. (2003) 198(3):483-489.
Mondal, A., et al., "IDO1 is an Integral Mediator of Inflammatory Neovascularization" EBioMedicine (2016) 14:74-82.
Smith, C., et al., "IDO Is a Nodal Pathogenic Driver of Lung Cancer and Metastasis Development" Cancer Discov. (2012) 2(8):722-35.
Connor, K.M., "Quantification of oxygen-induced retinopathy in the mouse: a model of vessel loss, vessel regrowth and pathological angiogenesis" Nat. Protoc. (2009) 4(11):1565-1573.
Lee, Y.M., et al., "Ethyl Pyruvate Inhibits Retinal Pathogenic Neovascularization by Downregulating HMGB1 Expression" J. Diabetes Res. (2013) 2013:245271.
Park, C.Y., et al., "The Role of Indoleamine 2,3-Dioxygenase in Retinal Pigment Epithelial Cell-mediated Immune Modulation" Ocular Immunol. Inflamm. (2010) 18(1):24-31.
Banerjee, T., et al., "A key in vivo antitumor mechanism of action of natural product-based brassinins is inhibition of indoleamine 2,3-dioxygenase" Oncogene (2008) 27:2851-2857.
Kumar, S., et al., "Indoleamine 2,3-Dioxygenase Is the Anticancer Target for a Novel Series of Potent Naphthoquinone-Based Inhibitors" J. Med. Chem. (2008) 51(6):1706-1718.

(Continued)

Primary Examiner — Samira J Jean-Louis
(74) Attorney, Agent, or Firm — Robert C. Netter, Jr.; Dann, Dorfman, Herrell & Skillman

(57) ABSTRACT

Compositions and methods for the treatment of ocular diseases are disclosed.

9 Claims, 5 Drawing Sheets

(56) References Cited

OTHER PUBLICATIONS

Prendergast, G.C., et al., "Indoleamine 2,3-dioxygenase pathways of pathgenic inflammation and immune escape in cancer" Cancer Immunol. Immunother. (2014) 63(7):721-735.

Prendergast, G.C., et al., "Indoleamine 2,3-dioxygenase as a Modifier of Pathogenic Inflammation in Cancer and other Inflammation-Associated Diseases" Curr. Med. Chem. (2011) 18(15):2257-2262.

* cited by examiner

1

METHODS AND COMPOSITIONS FOR THE TREATMENT OF RETINOPATHY AND OTHER OCULAR DISEASES

This application is a § 371 application of PCT/US2015/066737, filed Dec. 18, 2015, which claims priority under 35 U.S.C. § 119(e) to U.S. Provisional Patent Application No. 62/093,848, filed on Dec. 18, 2014. The foregoing applications are incorporated by reference herein.

FIELD OF THE INVENTION

This invention relates to the field of ocular diseases. Specifically, the invention provides novel compositions and methods for the treatment of ocular diseases, particularly ocular diseases characterized by abnormal vascularization such as retinopathy.

BACKGROUND OF THE INVENTION

Eye disease is a significant cause of morbidity in the U.S. and throughout the world. For example, retinopathy is one of the most common causes of vision loss in the world and age-related macular degeneration is the most common cause of blindness in people over 50 in the U.S. While therapies have improved for many eye diseases, there is still a need for methods and compositions for inhibiting or treating eye diseases, particularly those characterized by aberrant vascularization.

SUMMARY OF THE INVENTION

In accordance with one aspect of the instant invention, methods for treating, inhibiting (e.g., reducing), and/or preventing an ocular disease in a subject are provided. The methods comprise the administration of at least one inhibitor of the induction or activity of tryptophan degradation and/or of the downstream pathways that respond to this process. In a particular embodiment, the methods comprise the administration of an inhibitor of IDO1.

Compositions for the treatment of an ocular disease are also provided. The compositions comprise at least one inhibitor of the induction or activity of tryptophan degradation or of the downstream pathways that respond to this process (e.g., an inhibitor of IDO1) and at least one pharmaceutically acceptable carrier.

DETAILED DESCRIPTION OF THE INVENTION

Figure 1A:
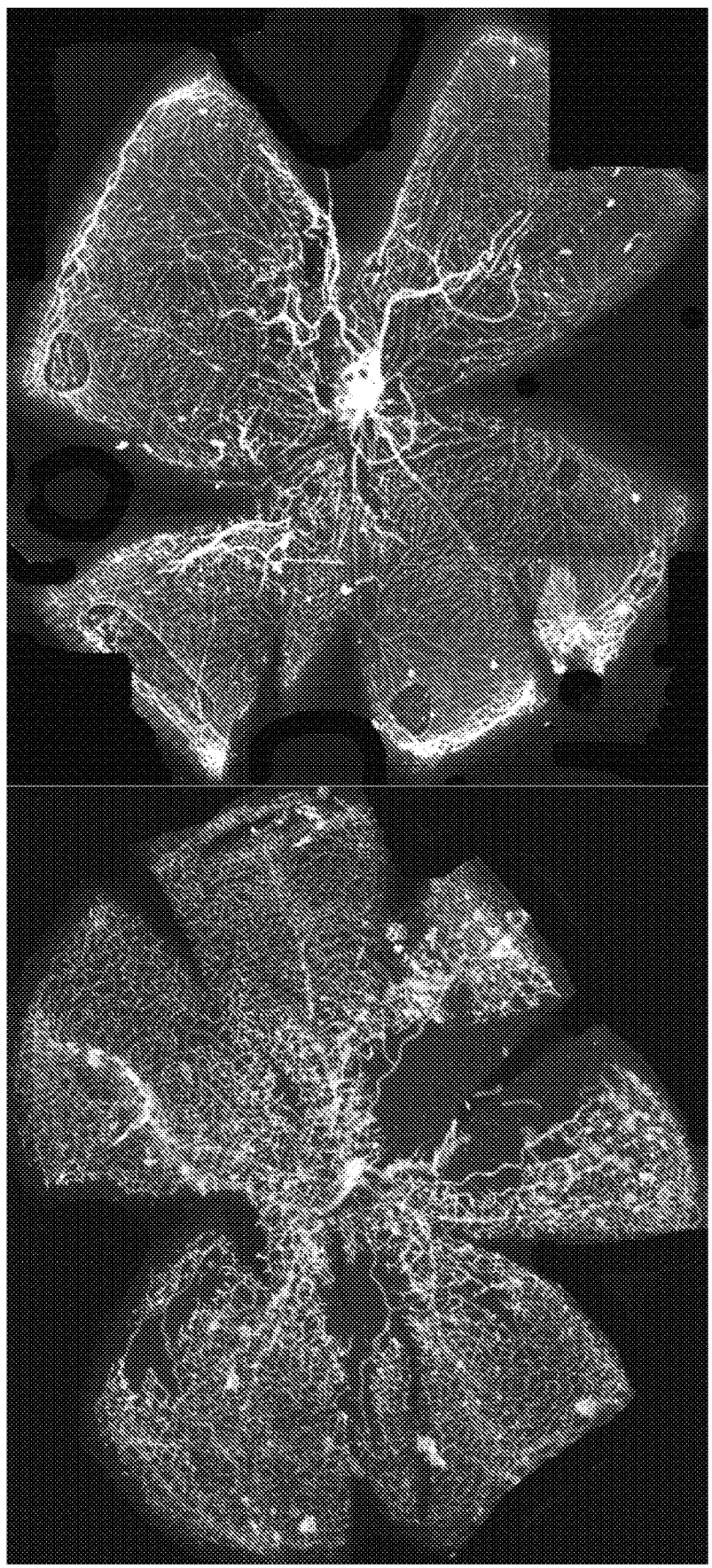
FIG. 1A provides images of retinal flat mounts from wild-type (left) and Ido1 knockout (Ido$^{-/-}$; right) mice at P17.

Indoleamine 2,3-dioxygenase 1 (IDO1) is an extrahepatic enzyme that catabolizes the essential amino acid tryptophan independent of metabolic processing of tryptophan in the liver. Detection of elevated levels of tryptophan catabolites in the urine of bladder cancer patients was first reported in the 1950's (Boyland et al. (1956) Biochem. J., 64:578-582; Boyland et al. (1955) Process. Biochem., 60:v). The determination that cancer-associated tryptophan catabolism was not attributable to elevated activity of TDO2, the liver enzyme responsible for maintaining tryptophan homeostasis (Gailani et al. (1973) Cancer Res., 33:1071-1077), led, in part, to the discovery of IDO1 from rabbit intestine (Higuchi et al. (1967) Arch. Biochem. Biophys., 120:397-403; Higuchi et al. (1963) Federation Proc., 22:243). The inflammatory cytokine IFNγ was found to be a major inducer of IDO1 (Yoshida et al. (1981) Proc. Natl. Acad. Sci., 78:129-132), and a general consensus initially formed around the idea of IDO1 elevation being a tumoricidal effect of IFNγ exposure that starves the rapidly growing tumor cells of this essential amino acid (Ozaki et al. (1988) Proc. Natl. Acad. Sci., 85:1242-1246). More recently, however, a major conceptual shift regarding IDO1 as a regulator of immune function has emerged from the finding that IDO1 activity could suppress cytotoxic T cell activation (Mellor et al. (1999) Immunol. Today 20:469-473; Munn et al. (1999) J. Exp. Med., 189: 1363-1372). The demonstration that administering the bioactive IDO1 pathway inhibitor 1-methyl-tryptophan (1MT) to pregnant mice could elicit T cell-dependent rejection of allogeneic mouse concepti (Munn et al. (1998) Science 281:1191-1193; Mellor et al. (2001) Nat. Immunol., 2:64-68) dramatically cemented the concept of IDO1 as an immunosuppressive actor and sparked the idea that tumors might appropriate this mechanism of protecting the 'foreign' fetus to overcome immunosurveillance. Experimental support for this concept has come from studies in a mouse skin epithelial tumor isograft model linking loss of the tumor suppressor gene Bin1 to IDO1 dysregulation and immune escape (Muller et al. (2005) Nat. Med., 11:312-319).

The historical focus in cancer research on oncogenes and tumor suppressor genes is based on the core assumption that tumorigenesis is essentially a cell autonomous process. IDO1, however, falls outside this conventional framework in that it can contribute to tumor development not only when it is expressed within tumor cells where immunoediting may be at play but also when it is expressed within the normal stroma. Specifically, its induction in antigen presenting cells, in particular dendritic cells and macrophages, has been implicated in promoting immune tolerance by suppressing effector T cells, converting naïve T cells to FoxP3$^+$ Tregs and elevating the suppressive activity of "natural" Tregs (Munn et al. (2013) Trends Immunol., 34:137-143). Extratumoral induction of IDO1 was first reported in the B16 melanoma tumor graft model in which no IDO1 was detectable in the tumors but was elevated in the tumor draining lymph nodes (TDLN) where it was localized to a specific subset of dendritic cells (Munn et al. (2004) J. Clin. Invest., 114:280-290). Several different IDO1 inhibitory compounds have since been identified that can produce highly significant B16 tumor growth suppression that is dependent both on intact T cell immunity and IDO1 function in the animal (Banerjee et al. (2008) Oncogene 27:2851-2857; Kumar et al. (2008) J. Med. Chem., 51:1706-1718; Muller et al. (2010) Cancer Res., 70:1845-1853). In the classical two stage skin carcinogenesis, an autochthonous tumor model not involving the inherently artificial engrafting of tumor cells, it has been shown that genetic loss of IDO1 rendered mice resistant to papilloma development (Muller et al. (2008) Proc. Natl. Acad. Sci., 105:17073-17078). No evidence of IDO1 was found in the developing lesions but rather again in the TDLN (Muller et al. (2008) Proc. Natl. Acad. Sci., 105:17073-17078). In this context where tumor initiation and promotion are distinctly separable, IDO1 in the TDLN was found to be elevated in the tumor-promoting inflammatory environment irrespective of tumor initiation.

Whereas IDO1 elevation in tumor cells may be selected as an escape mechanism during immunoediting, skin carcinogenesis data suggested that elevated extratumoral IDO1 expression preceding tumor initiation can direct the immune environment to be more pro-tumorigenic. To test this idea further, the development of tumors in the lungs was studied as this is an organ in which the constitutive level of IDO1 is relatively high (Takikawa et al. (1986) J. Biol. Chem., 261:3648-3653). Genetic loss of IDO1 resulted in a marked decrease in the pulmonary tumor burden in both a transgenic mouse model of de novo lung carcinoma as well as in an orthotopic graft model of metastatic breast cancer. In both instances this translated to a significant survival benefit in the Ido1$^{-/-}$ animals (Smith et al. (2012) Cancer Discov., 2:722-735). Unexpectedly, vascularization in the lung was significantly reduced with the loss of IDO1 (Smith et al. (2012) Cancer Discov., 2:722-735). This result suggests the possibility that IDO1 may have a role in supporting angiogenesis. This would be consistent with its physiological role in maintaining pregnancy, as the inflammatory environment elicited by implantation in the endometrium directs angiogenesis as well as immune tolerance (Holtan et al. (2011) Front. Biosci., 3:1533-1540).

Angiogenesis is critical to tumor development (Cao et al. (2011) Sci. Transl. Med., 3(114):114rv113). Unlike physiologic angiogenesis which is tightly regulated, in cancer there is excessive and disorganized growth of blood vessels much like that induced by ischemia in tissues such as the retina and lungs. In experimental models of ischemia, immune cells have been shown to be important for pruning the excess vasculature and limiting neovascularization (Ishida et al. (2003) Nat. Med., 9:781-788; Wagner et al. (2008) Am. J. Physiol. Lung Cell. Mol. Physiol., 294:L351-357), suggesting that immunity might play an important anti-angiogenic role in tumors as well. In particular, IFNγ, an inflammatory cytokine, long recognized as a major inducer of IDO1, has been shown to exert angiostatic activity against developing tumors. Indeed, angiostasis elicited by IFNγ, rather than direct tumor cell killing, has been implicated as being the primary mechanism for both CD4 and CD8 T cell-mediated tumor rejection (Qin et al. (2000) Immunity 12:677-686; Qin et al. (2003) Cancer Res., 63:4095-4100). In this context, the finding that loss of IDO1 resulted in diminished pulmonary vascularization (Smith et al. (2012) Cancer Discov., 2:722-735) suggested the hypothesis that IDO1 induced by IFNγ might be working at cross purposes to limit IFNγ-mediated angiostasis and that this might be an important factor accounting for the ability of IDO1 to promote tumor outgrowth. In this same study (Smith et al. (2012) Cancer Discov., 2:722-735), IDO1 loss was associated with attenuated induction of the cytokine IL6 which is known to be pro-angiogenic and has been shown to be important for ischemia-induced neovascularization in the lungs (McClintock et al. (2005) J. Appl. Physiol., 99:861-866). In a model of pulmonary metastasis, ectopic expression of IL6 could overcome the resistance exhibited by Ido1$^{-/-}$ mice, supporting the biological relevance of the regulatory impact that IDO1 exerts on IL6 in a setting of pulmonary tumor outgrowth. These findings lead to a novel conceptual paradigm whereby elevated IDO in the host environment acts downstream of IFNγ-mediated angiostasis and upstream of IL6-mediated angiogenesis from the very onset of tumor initiation to shift the immune response towards tumor promotion.

In order to directly test whether IDO1 supports pathologic angiogenesis, a mouse model of oxygen-induced retinopathy (OIR) (Connor et al. (2009) Nat. Protoc., 4:1565-1573) has been studied. As in cancer, inflammatory stimuli drive neovascularization in proliferative retinopathy and the OIR model has proved to be a temporally defined and quantifiable surrogate system for studying the factors involved in tumor angiogenesis (Palmer et al. (2012) Br. J. Pharmacol., 165:1891-1903; Stahl et al. (2012) Blood 120:2925-2929). As shown herein, pathological neovascularization in the OIR model was significantly reduced in Ido1 knockout mice (Ido1$^{-/-}$) mice or mice treated with inhibitors of IDO1 or the IDO pathway (e.g., inhibitory nucleic acid molecules (e.g., siRNA)), whereas normal retinal vascular development under normoxic conditions was unaffected in the Ido1$^{-/-}$ mice. Likewise, the physiological revascularization that occurs in response to ischemia was not impaired and even appears to have been enhanced as a result of IDO1 loss as assessed by the relative sizes of the avascular areas. Thus, IDO1 inhibitors can overcome the indiscriminate targeting of normal compensatory revascularization that is a detrimental consequence of current anti-VEGF antibody therapy. Consistent with IDO1 supporting neovascularization primarily by counteracting the angiostatic activity of IFNγ, the concurrent elimination of IFNγ in double knockout IFNγ$^{-/-}$ Ido1$^{-/-}$ mice reverted the level of neovascularization in the OIR model back to wild type levels. Conversely, IL6$^{-/-}$ mice exhibited a reduction in neovascularization similar to that observed in Ido1$^{-/-}$ mice consistent with IDO1 acting upstream to potentiate the angiogenic activity of IL6.

The present invention provides compositions and methods for the inhibition, prevention, and/or treatment of ocular diseases. The present invention also provides compositions and methods for the inhibition, prevention, and/or treatment of abnormal neovascularization (e.g., in the eye). The present invention also provides compositions and methods for increasing and/or promoting normal vascularization and/or vascular growth (e.g., in the eye). The methods comprise administering at least one inhibitor of the induction or activity of tryptophan degradation or of the downstream pathways that respond to this process to a subject. In a particular embodiment, the inhibitor is a small molecule inhibitor. In a particular embodiment, the inhibitor is an inhibitory nucleic acid molecule (e.g., antisense, siRNA, shRNA, etc.) or a vector encoding the same. In a particular embodiment, the inhibitor is an antibody or antibody fragment immunologically specific for the protein to be inhibited (e.g., a neutralizing antibody). In a particular embodiment, the methods comprise the administration of an IDO1 and/or IDO2 (see, e.g., PCT/US07/69271) inhibitor. In a particular embodiment, the method comprises the administration of an IDO1 inhibitor.

The inhibitors of the instant invention may inhibit the induction and/or activity of tryptophan degradation and/or of the downstream pathways that respond to this process. In a particular embodiment, the inhibitor of the instant invention inhibits the expression, induction, and/or activity of IDO1 and/or of the downstream pathways from IDO1. The IDO1 inhibitors may directly interfere with IDO1 activity, inhibit induction of IDO1, or act as an inhibitor of the activation of downstream signaling pathways. In a particular embodiment, the IDO1 inhibitor is an antibody immunologically specific for IDO1. Examples of IDO1 inhibitors are provided, without limitation, in PCT/US2014/022680 (e.g., tricyclic compounds related to imidazoisoindoles; compounds of Formulas I-V), PCT/US2012/033245 (e.g., fused imidazole derivatives; compounds of Formula I or II), PCT/US2010/054289 (e.g., imidazole derivatives; compounds of Formulas I-VIII), PCT/US2009/041609 (e.g., compounds of Formulas I-VIII), PCT/US2008/57032 (e.g., napthoquinone derivatives; compounds of Formula I, II, or III), PCT/US2008/085167 (e.g., compounds of Formulas I-XLIV), PCT/US2006/42137 (e.g., compounds of Formula I), PCT/US2004/005155 (e.g., phenyl-TH-DL-trp (3-(N-phenyl-thiohydantoin)-indole), propenyl-TH-DL-trp (3-(N-allyl-thiohydantoin)-indole), and methyl-TH-DL-trp (3-(N-methyl-thiohydantoin)-indole)), PCT/US2004/005154 (e.g., compounds of Formula I or II), U.S. Pat. No. 7,705,022 (e.g., compounds of Formula I), U.S. Pat. No. 8,008,281 (e.g., phenyl-TH-DL-trp (3-(N-phenyl-thiohydantoin)-indole), propenyl-TH-DL-trp (3-(N-allyl-thiohydantoin)-indole), and methyl-TH-DL-trp (3-(N-methyl-thiohydantoin)-indole)), U.S. Pat. No. 7,714,139 (e.g., compounds of Formula I or II), U.S. Patent Application Publication No. 20140066625 (e.g., fused imidazole derivatives; compounds of Formula I or II), U.S. Patent Application Publication No. 20130177590 (e.g., N-hydroxyamidinoheterocycles; compounds of Formulas U.S. Patent Application Publication No. 20140023663 (e.g., 1,2,5-oxadiazoles; compounds of Formula I), U.S. Patent Application Publication No. 20080146624 (e.g., amidines; compounds of Formulas I or II), U.S. Patent Application Publication No. 20080119491 (e.g., amidinoheterocycles; compounds of Formulas I-IV), U.S. Patent Application Publication No. 20080182882 (e.g., N-hydroxyamidinoheterocycles; compounds of Formula I), U.S. Patent Application Publication No. 20080214546 (e.g., N-hydroxyamidinoheterocycles; compounds of Formula I), U.S. Patent Application Publication No. 20060258719 (compounds of Formula I), Banerjee et al. (2008) Oncogene 27:2851-2857 (e.g., brassinin derivatives;), and Kumar et al. (2008) J. Med. Chem., 51:1706-1718 (e.g., phenyl-imidazole-derivatives). All references are incorporated by reference herein, particularly for the IDO1 inhibitors provided therein.

Inhibitors of IDO1 expression include, without limitation, inhibitors of JAK/STAT (e.g., JAK, STAT3, STAT1) (Du et al. (2000) J. Interferon Cytokine Res., 20:133-142, Muller et al. (2005) Nature Med., 11:312-319; Yu et al. (2014) J. Immunol., 193:2574-2586), NFκB (Muller et al. (2005) Nature Med., 11:312-319; Muller et al. (2010) Cancer Res., 70:1845-1853), KIT (Balachandran et al. (2011) Nature Med., 17:1094-1100), MET (Rutella et al. (2006) Blood 108:218-227; Giannoni et al. (2014) Haematologica 99:1078-1087), RAS/RAF/MEK (Liu (2010) Blood 115: 3520-3530), aryl hydrocarbon receptor (AHR) (Bessede et al. (2014) Nature 511:184-190; Litzenburger et al. (2014) Oncotarget 5:1038-1051), or vascular endothelial growth factor receptor (VEGFR) (Marti et al. (2014) Mem Inst Oswaldo Cruz 109:70-79). In a particular embodiment, the inhibitor is not an inhibitor of VEGFR.

Inhibitors of IDO1 downstream signaling include, without limitation, inhibitors of GCN2 (Munn et al. (2005) Immunity 22:633-642; Muller (2008) Proc Nat Acad Sci., 105: 17073-17078), C/EBP homologous protein 10 (CHOP-10; also known as gadd153; herein referred to as CHOP; Munn et al. (2005) Immunity 22:633-642), activating-transcription factor 4 (ATF4; Munn et al. (2005) Immunity 22:633-642; Thevenot et al. (2014) Immunity 41:389-401), or aryl hydrocarbon receptor (AHR) (Opitz et al. (2011) Nature 478:197-203; Litzenburger et al. (2014) Oncotarget 5:1038-1051); or activators of mammalian target of rapamycin (mTOR) or protein kinase C (PKC)-Θ (Metz et al. (2012) Oncoimmunology 1:1460-1468). In a particular embodiment, the inhibitor of IDO1 downstream signaling is an inhibitor of IL6 (e.g., an antibody immunologically specific for IL6).

In a particular embodiment, the IDO1 inhibitor is not ethyl pyruvate. In a particular embodiment, the IDO1 inhibitor (e.g., inhibitor of downstream signaling pathway) is 1-methyl-tryptophan, particularly 1-methyl-D-tryptophan or a racemic mix comprising the same. In a particular embodiment, the IDO inhibitor is 1-methyl-tryptophan, epacadosat (Incyte), or GDC-0919 (NewLink Genetics/Genentech).

In a particular embodiment, the ocular disease is characterized by abnormal/aberrant vascularization. In a particular embodiment the ocular disease is characterized by intraocular neovascularization. The intraocular neovascularization may be, without limitation, neovascularization of the optic disc, iris, retina, choroid, cornea, and/or vitreous humour. Examples of ocular diseases include, without limitation, glaucoma, pannus, pterygium, macular edema, macular degeneration (e.g., age-related macular degeneration), retinopathy (e.g., diabetic retinopathy, vascular retinopathy, retinopathy of prematurity), diabetic retinal ischemia, diabetic macular edema, retinal degeneration, retrolental fibroplasias, retinoblastoma, corneal graft neovascularization, central retinal vein occlusion, pathological myopia, ocular tumors, uveitis, inflammatory diseases of the eye, and proliferative vitreoretinopathy. In a particular embodiment, the ocular disease is selected from the group consisting of retinopathy (e.g., retinopathy of prematurity, diabetic retinopathy (e.g., proliferative diabetic retinopathy)) and macular degeneration (e.g., wet macular degeneration).

As used herein, the term "macular degeneration" refers to ocular diseases wherein the macula—a small and highly sensitive part of the retina responsible for detailed central vision—degenerates and/or loses functional activity. The degeneration and/or loss of functional activity may be due to any reason including, without limitation, cell death or apoptosis, decreased cell proliferation, and/or loss of normal biological function. Macular degeneration may be wet (exudative or neovascular) or dry (non-exudative, atrophic or non-neovascular). In a particular embodiment, the instant invention encompasses the treatment of wet macular degeneration. Wet macular degeneration is typically characterized by the formation of new vessels to improve the delivery of blood to oxygen deprived retinal tissue (although the new vessels typically rupture, causing bleeding and damage to surrounding tissue). Examples of macular degeneration diseases include, without limitation, age-related macular degeneration and Sorsby fundus dystrophy.

As used herein, the term "diabetic retinopathy" refers to changes in the retina due to microvascular (e.g., retinal and choroidal) changes associated with diabetes. Without being bound by theory, small blood vessels within the retina, which are particularly susceptible to poor blood glucose control, are damaged due to long-term exposure to high levels of blood sugar (hyperglycemia). Diabetic retinopathy may affect one or both eyes, typically both eyes. The term "diabetic retinopathy" encompasses mild, moderate, or severe non-proliferative (simple) diabetic retinopathy (NPDR) and proliferative diabetic retinopathy (PDR). In a particular embodiment, the instant invention encompasses the treatment of proliferative diabetic retinopathy. Proliferative diabetic retinopathy is typically characterized by the formation of new vessels to improve the delivery of blood to oxygen deprived retinal tissue.

As used herein, the term "retinopathy of prematurity", which is also known as Terry syndrome or retrolental fibroplasia, refers to abnormal blood vessel development in the retina of the eye that occurs in infants that are born prematurely. Retinopathy of prematurity is typically characterized by fibrovascular proliferation and the growth of abnormal new vessels.

Based on the data provided herein, it is clear that the functional loss of IDO1 dramatically resolves abnormal neovascularization but has no discernable negative impact on normal vascular development. Notably, IDO1 inhibitors can be small molecules, which can allow for their administration to the eye via eye drops. This is in contrast to current anti-VEGF antibody therapies which require intravitreal injections.

Compositions comprising at least one inhibitor of the induction or activity of tryptophan degradation or of the downstream pathways that respond to this process (e.g., an IDO1 inhibitor) are also encompassed by the instant invention. In a particular embodiment, the composition comprises at least one inhibitor and at least one pharmaceutically acceptable carrier. The composition may further comprise at least one other therapeutic compound for the inhibition, treatment, and/or prevention of the ocular disease or disorder (see, e.g., hereinbelow). Alternatively, at least one other therapeutic compound may be contained within a separate composition(s) with at least one pharmaceutically acceptable carrier. The present invention also encompasses kits comprising a first composition comprising at least one inhibitor and a second composition comprising at least one other therapeutic compound for the inhibition, treatment, and/or prevention of the ocular disease or disorder. The first and second compositions may further comprise at least one pharmaceutically acceptable carrier.

The compositions of the instant invention are useful for treating an ocular disease in a subject, particularly an ocular disease characterized by abnormal vascularization. A therapeutically effective amount of the composition may be administered to the subject. The dosages, methods, and times of administration are readily determinable by persons skilled in the art, given the teachings provided herein.

The compositions of the present invention can be administered by any suitable route. In a particular embodiment, the compositions are administered directly to the site of treatment (e.g., site for inhibiting abnormal neovascularization). In a particular embodiment, the compositions described herein are administered in any way suitable to effectively achieve a desired therapeutic effect in the eye. For example, the compositions of the instant invention may be administered locally to the eye, such as by topical administration, injection, or delivery by an implantable device. Methods of administration include, without limitation, topical, intraocular (including intravitreal), transdermal, oral, intravenous, subconjunctival, subretinal, or peritoneal routes of administration. The compositions of the instant invention can be in any form applicable for ocular administration. For example, the compositions may be in the form of eye drops, sprays, creams, ointments, gels (e.g., hydrogels), lens, films, implants, solutions, suspensions, and colloidal systems (e.g. liposomes, emulsions, dendrimers, micelles etc.). The compositions may also be modified to increase the residence time of the compounds in the eye, provide a sustained release of compounds, and/or avoid toxicity and increase ocular tolerability.

In general, the pharmaceutically acceptable carrier of the composition is selected from the group of diluents, preservatives, solubilizers, emulsifiers, adjuvants and/or carriers. The compositions can include diluents of various buffer content (e.g., Tris-HCl, acetate, phosphate), pH and ionic strength; and additives such as detergents and solubilizing agents (e.g., polysorbate 80), anti-oxidants (e.g., ascorbic acid, sodium metabisulfite), preservatives (e.g., Thimersol, benzyl alcohol) and bulking substances (e.g., lactose, mannitol). In a particular embodiment, the carrier is an aqueous or saline carrier. The compositions can also be incorporated into particulate preparations of polymeric compounds such as polylactic acid, polyglycolic acid, etc., or into liposomes or nanoparticles. Such compositions may influence the physical state, stability, rate of in vivo release, and rate of in vivo clearance of components of a pharmaceutical composition of the present invention. See, e.g., Remington's Pharmaceutical Sciences, (Mack Publishing Co., Easton, Pa.). The pharmaceutical composition of the present invention can be prepared, for example, in liquid form, or can be in dried powder form (e.g., lyophilized) for reconstitution prior to administration. In a particular embodiment, the composition is an aqueous formulation with a pH physiologically compatible with the eye (e.g., a pH in the range from about 5.5 to about 8, particularly from about 6.0 to about 7.5). In a particular embodiment, the composition is an aqueous formulation having isotonic and physiological characteristics suitable for ocular administration.

The methods of the instant invention may further comprise monitoring the ocular disease or disorder in the subject after administration of the composition(s) of the instant invention to monitor the efficacy of the method. For example, the subject may undergo an appropriate eye exam to determine the severity of the ocular disease or disorder (e.g., to determine if the severity of the ocular disease or disorder has lessened).

The methods of the instant invention may further comprise the administration of at least one other therapeutic method for the treatment of the ocular disease or disorder and/or the administration of at least one other therapeutic compound for the treatment of the ocular disease or disorder. Methods of treating ocular diseases, particular ocular disease characterized by abnormal vascularization, may also be treated with one or more additional therapies including, without limitation, laser therapy (e.g., laser photocoagulation and photodynamic therapy (e.g., administration of verteporfin and application of light of the correct wavelength to activate verteporfin and obliterate the vessels)) and cryotherapy (freezing). With regard to diabetic retinopathy, compounds and/or therapies which inhibit and/or treat the underlying diabetic condition may also be used. For example, compounds (e.g., insulin, metformin, meglumine, sorbitol) and methods which maintain optimal blood sugar levels can be administered to the subject.

As stated hereinabove, the compositions and methods of the instant invention may further comprise one or more other compounds of methods that treat an ocular disease. In a particular embodiment, the further compound modulates ocular vascularization. Examples of other therapeutic compounds include, without limitation, corticosteroids (e.g., triamcinolone (e.g., intravitreal triamcinolone acetonide)), angiogenesis inhibitors, anti-vascular endothelial growth factor (VEGF) antibodies or compounds (e.g., anti-VEGF-A antibodies, ranibizumab, bevacizumab, WO 2014/056923), anti-vascular endothelial growth factor aptamers (e.g., pegaptanib), vascular endothelial growth factor inhibitors (e.g., aflibercept), and anecortave acetate.

Definitions

The following definitions are provided to facilitate an understanding of the present invention:

The singular forms "a," "an," and "the" include plural referents unless the context clearly dictates otherwise.

A "therapeutically effective amount" of a compound or a pharmaceutical composition refers to an amount effective to prevent, inhibit, treat, or lessen the symptoms of a particular disorder or disease. The treatment of an ocular disorder herein may refer to curing, relieving, and/or preventing the ocular disorder, the symptom of it, or the predisposition towards it.

"Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a diluent, adjuvant, excipient, auxiliary agent or vehicle with which an active agent of the present invention is administered. Pharmaceutically acceptable carriers can be sterile liquids, such as water and oils, including those of petroleum, animal, vegetable or synthetic origin, such as peanut oil, soybean oil, mineral oil, sesame oil and the like. Water or aqueous saline solutions and aqueous dextrose and glycerol solutions are preferably employed as carriers, particularly for injectable solutions. Suitable pharmaceutical carriers are described, for example, in "Remington's Pharmaceutical Sciences" by E. W. Martin.

As used herein, the term "prevent" refers to the prophylactic treatment of a subject who is at risk of developing a condition resulting in a decrease in the probability that the subject will develop the condition.

The term "treat" as used herein refers to any type of treatment that imparts a benefit to a patient afflicted with a disease, including improvement in the condition of the patient (e.g., in one or more symptoms), delay in the progression of the condition, etc.

As used herein, the terms "host," "subject," and "patient" refer to any animal, including mammals such as humans.

As used herein, the term "small molecule" refers to a substance or compound that has a relatively low molecular weight (e.g., less than 2,000). Typically, small molecules are organic, but are not proteins, polypeptides, or nucleic acids.

The phrase "small, interfering RNA (siRNA)" refers to a short (typically less than 30 nucleotides long, particularly 12-30 or 20-25 nucleotides in length) double stranded RNA molecule. Typically, the siRNA modulates the expression of a gene to which the siRNA is targeted. Methods of identifying and synthesizing siRNA molecules are known in the art (see, e.g., Ausubel et al. (2006) Current Protocols in Molecular Biology, John Wiley and Sons, Inc). As used herein, the term siRNA may include short hairpin RNA molecules (shRNA). Typically, shRNA molecules consist of short complementary sequences separated by a small loop sequence wherein one of the sequences is complimentary to the gene target. shRNA molecules are typically processed into an siRNA within the cell by endonucleases. Exemplary modifications to siRNA molecules are provided in U.S. Application Publication No. 20050032733. Expression vectors for the expression of siRNA molecules preferably employ a strong promoter which may be constitutive or regulated. Such promoters are well known in the art and include, but are not limited to, RNA polymerase II promoters, the T7 RNA polymerase promoter, and the RNA polymerase III promoters U6 and H1 (see, e.g., Myslinski et al. (2001) Nucl. Acids Res., 29:2502 09).

"Antisense nucleic acid molecules" or "antisense oligonucleotides" include nucleic acid molecules (e.g., single stranded molecules) which are targeted (complementary) to a chosen sequence (e.g., to translation initiation sites and/or splice sites) to inhibit the expression of a protein of interest. Such antisense molecules are typically between about 15 and about 50 nucleotides in length, more particularly between about 15 and about 30 nucleotides, and often span the translational start site of mRNA molecules. Antisense constructs may also be generated which contain the entire sequence of the target nucleic acid molecule in reverse orientation. Antisense oligonucleotides targeted to any known nucleotide sequence can be prepared by oligonucleotide synthesis according to standard methods.

An "antibody" or "antibody molecule" is any immunoglobulin, including antibodies and fragments thereof, that binds to a specific antigen. As used herein, antibody or antibody molecule contemplates intact immunoglobulin molecules, immunologically active portions of an immunoglobulin molecule, and fusions of immunologically active portions of an immunoglobulin molecule.

The antibody may be a naturally occurring antibody or may be a synthetic or modified antibody (e.g., a recombinantly generated antibody; a chimeric antibody; a bispecific antibody; a humanized antibody; a camelid antibody; and the like). The antibody may comprise at least one purification tag. In a particular embodiment, the framework antibody is an antibody fragment. Antibody fragments include, without limitation, immunoglobulin fragments including, without limitation: single domain (Dab; e.g., single variable light or heavy chain domain), Fab, Fab', F(ab')$_2$, and F(v); and fusions (e.g., via a linker) of these immunoglobulin fragments including, without limitation: scFv, scFv$_2$, scFv-Fc, minibody, diabody, triabody, and tetrabody. The antibody may also be a protein (e.g., a fusion protein) comprising at least one antibody or antibody fragment.

The antibodies of the instant invention may be further modified. For example, the antibodies may be humanized. In a particular embodiment, the antibodies (or a portion thereof) are inserted into the backbone of an antibody or antibody fragment construct. For example, the variable light domain and/or variable heavy domain of the antibodies of the instant invention may be inserted into another antibody construct. Methods for recombinantly producing antibodies are well-known in the art. Indeed, commercial vectors for certain antibody and antibody fragment constructs are available.

The antibodies of the instant invention may also be conjugated/linked to other components. For example, the antibodies may be operably linked (e.g., covalently linked, optionally, through a linker) to at least one cell penetrating peptide, detectable agent, imaging agent, or contrast agent. The antibodies of the instant invention may also comprise at least one purification tag (e.g., a His-tag). In a particular embodiment, the antibody is conjugated to a cell penetrating peptide.

As used herein, the term "immunologically specific" refers to proteins/polypeptides, particularly antibodies, that bind to one or more epitopes of a protein or compound of interest, but which do not substantially recognize and bind other molecules in a sample containing a mixed population of antigenic biological molecules.

A "cell-penetrating peptide" refers to a peptide which can transduce another peptide, protein, or nucleic acid into a cell in vitro and/or in vivo—i.e., it facilitates the cellular uptake of molecules. Examples of cell penetrating peptides include, without limitation, Tat peptides, penetratin, transportan, and the like.

The following examples are provided to illustrate various embodiments of the present invention. They are not intended to limit the invention in any way.

Example 1

Based on the observation that Ido1 knockout mice exhibit reduced blood vessel density in the lungs, the impact of the genetic loss of IDO1 in an oxygen-induced retinopathy (OIR) model was evaluated in order to determine if IDO1 has a role in supporting angiogenesis. The OIR model is a reliable, temporally defined, and quantifiable system for studying neovascularization over a period of 17 days. Like tumors, proliferative retinopathy is characterized by excessive and disorganized growth of pathologic blood vessels. Tumor angiogenesis studies have previously incorporated OIR as a surrogate model system.

The OIR is schematically presented in Connor et al. (Nat Protoc. (2009) 4:1565-73; FIG. 1). Briefly, mice were placed in a Plexiglas® chamber connected to an oxygen delivery system that provided a hyperoxic environment, which causes vessel regression in the central retina and cessation of normal radial vessel growth. Animals were kept in the hyperoxic environment in the chamber from postnatal (p) day 7 until P12 and then returned to atmospheric levels of oxygen (21%). Animals were sacrificed at P17—the peak of neovascularization—and their eyes were enucleated. The retinas were then extracted and labeled with FITC-lectin to fluorescently stain retinal vasculature and to quantitatively analyze neovascularization.

Figure 1B:
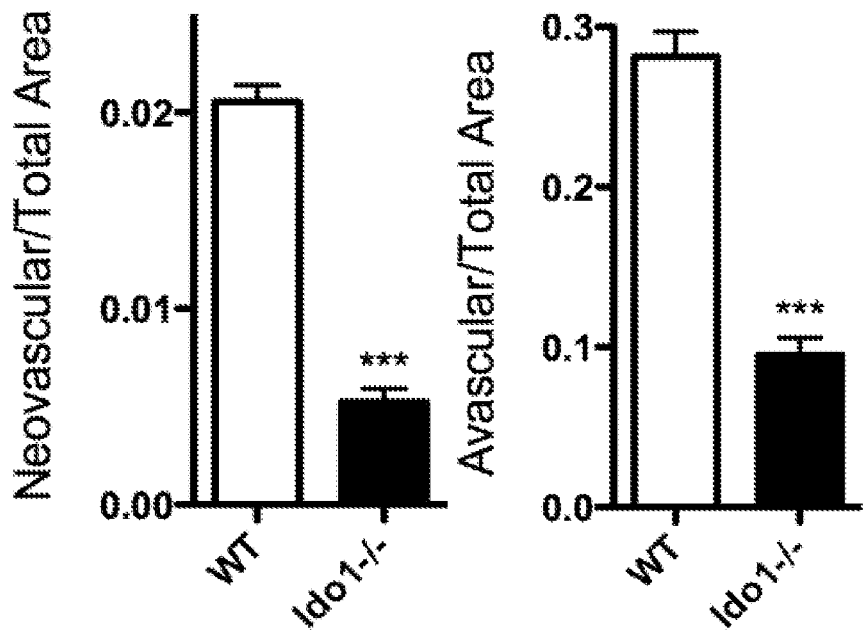
FIG. 1B provides a graph of the neovascularization observed in the retina from wild-type (WT) and Ido1 knockout (Ido$^{-/-}$) mice at P17 (left) and a graph of the avascular region observed in the retina from wild-type (WT) and Ido1 knockout (Ido$^{-/-}$) mice at P17 (right). Data are +/−SEM; N≥24/group; ***P<0.0001.

Representative microscopic images of FITC-lectin stained retinal flat mounts from wild type (WT) and Ido1 knockout (Ido1$^{-/-}$) mice at P17 are shown in FIG. 1A. It was readily apparent just from the images that the extent of neovascularization was markedly reduced in the eyes from Ido1$^{-/-}$ mice. Quantitative comparison between the two groups, shown in FIG. 1B (left panel), confirmed that there was a highly significant reduction in neovascularization in the mice lacking IDO1 (P<0.0001). Control animals maintained under normoxic conditions throughout the experiment demonstrated no appreciable evidence of abnormal neovascularization and the normal vascular development that occurred was indistinguishable between WT and Ido1$^{-/-}$ animals. In contrast to the reduction in abnormal neovascularization that resulted from the loss of IDO1, the significant (P=0.002) reduction in the avascular region observed in Ido1$^{-/-}$ animals relative to their wild type counterparts, shown in FIG. 1B (right panel), is indicative of an improvement in normal vascular regrowth occurring in mice lacking IDO1.

Figure 2A:
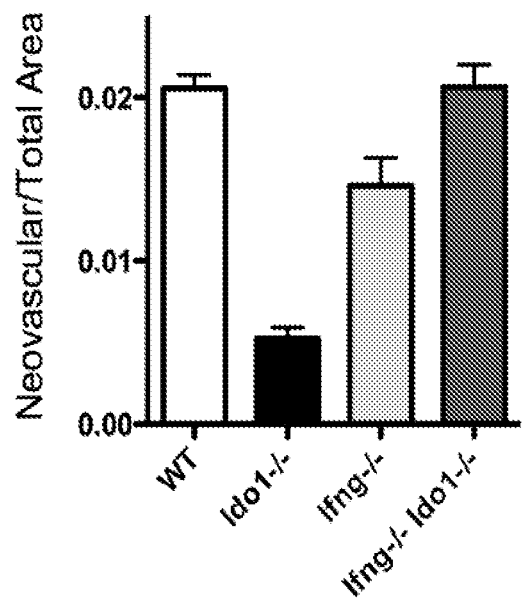
FIG. 2A provides a graph of the neovascularization observed in the retina from wild-type (WT), Ido1 knockout (Ido$^{-/-}$), IFN-γ knockout (Ifng$^{-/-}$), and double knockout (Ifng$^{-/-}$ Ido$^{-/-}$) mice at P17.
Figure 2B:
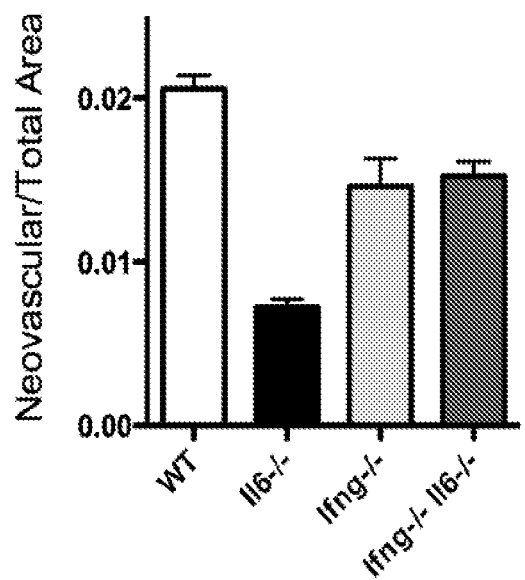
FIG. 2B provides a graph of the neovascularization observed in the retina from wild-type (WT), IL6 knockout (Il6$^{-/-}$), IFN-γ knockout (Ifng$^{-/-}$), and double knockout (Ifng$^{-/-}$ Il6$^{-/-}$) mice at P17.

IFNγ, an inflammatory cytokine, long recognized as a major inducer of IDO1, has been shown to exert angiostatic activity against developing tumors, which was implicated in these studies as the primary mechanism for both CD4 and CD8 T cell dependent tumor rejection. The loss of IDO1 results in diminished pulmonary vascularization (Smith et al. (2012) Cancer Discovery 2:722-735), suggesting that IDO1 might be working at cross purposes to limit IFNγ-mediated angiostasis. In this same study, IDO1 loss was also associated with the attenuated induction of the pro-angiogenic inflammatory cytokine IL6, suggesting that IDO1 might be acting upstream of IL6 to promote angiogenesis. Consistent with IDO1 supporting neovascularization primarily by counteracting the angiostatic activity of IFNγ, the concurrent elimination of IFNγ in double knockout Ifng$^{-/-}$ Ido1$^{-/-}$ mice reverted the level of neovascularization in the OIR model back to wild type levels (FIG. 2A). Conversely, Il6$^{-/-}$ mice exhibited a reduction in neovascularization in the OIR model similar to that observed in Ido1$^{-/-}$ mice, which was likewise reversed by the concurrent elimination of IFNγ in double knockout Ifng$^{-/-}$ Il6$^{-/-}$ mice (FIG. 2B), consistent with IDO1 acting upstream to potentiate the angiogenic activity of IL6 as an important contributing factor in IDO1's ability to support neovascularization.

Example 2

Figure 3:
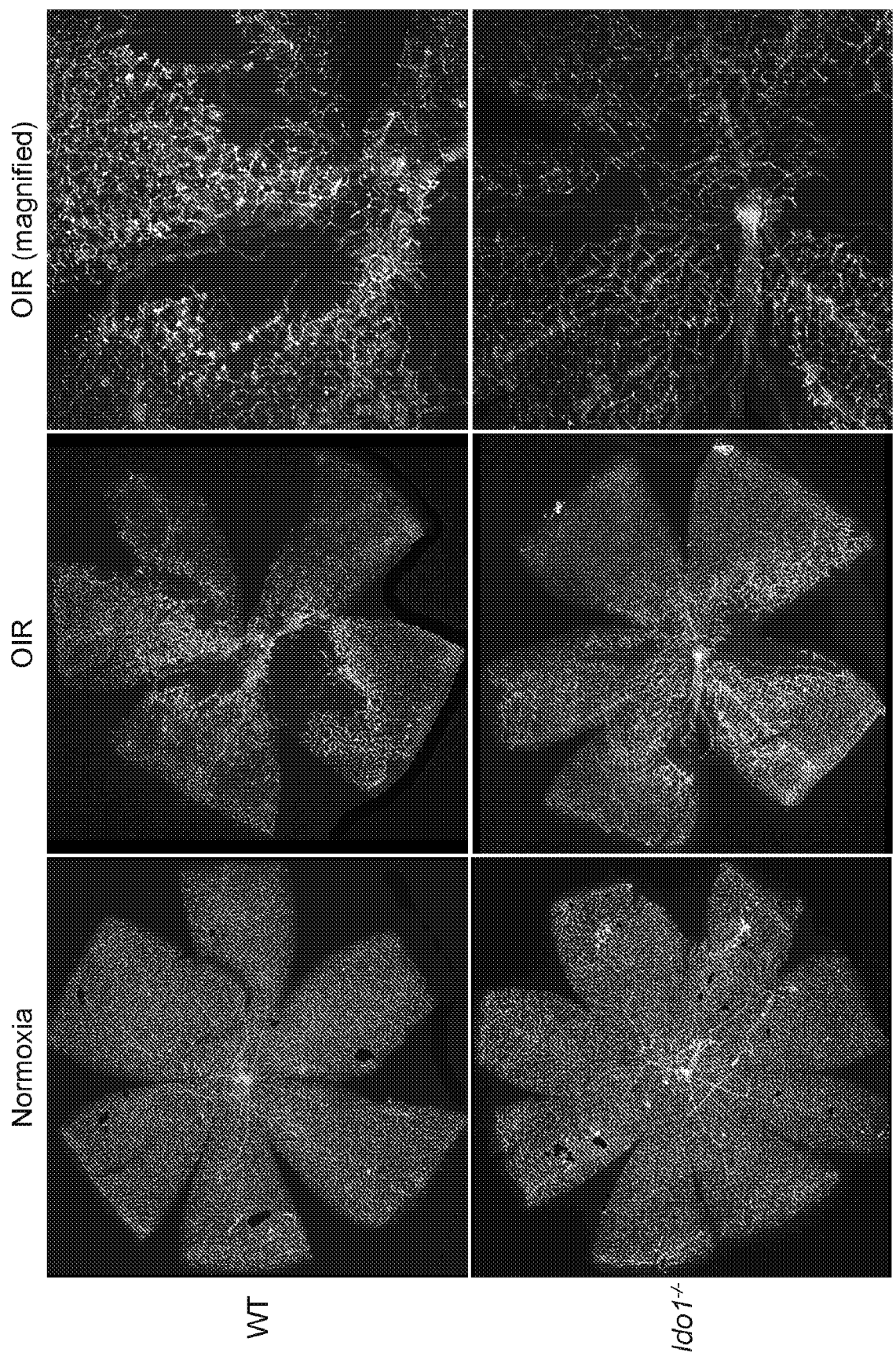
FIG. 3 provides representative images of isolectin staining of the vasculature in retinal flat mounts at P17 from WT and Ido1$^{-/-}$ neonates maintained either under constant normoxia (left column) or exposed to hyperoxia from P7-P12 to trigger oxygen-induced retinopathy (OIR; middle column). Right column (OIR (magnified)) provides higher magnifications of the OIR images in the middle column.
Figure 4A:
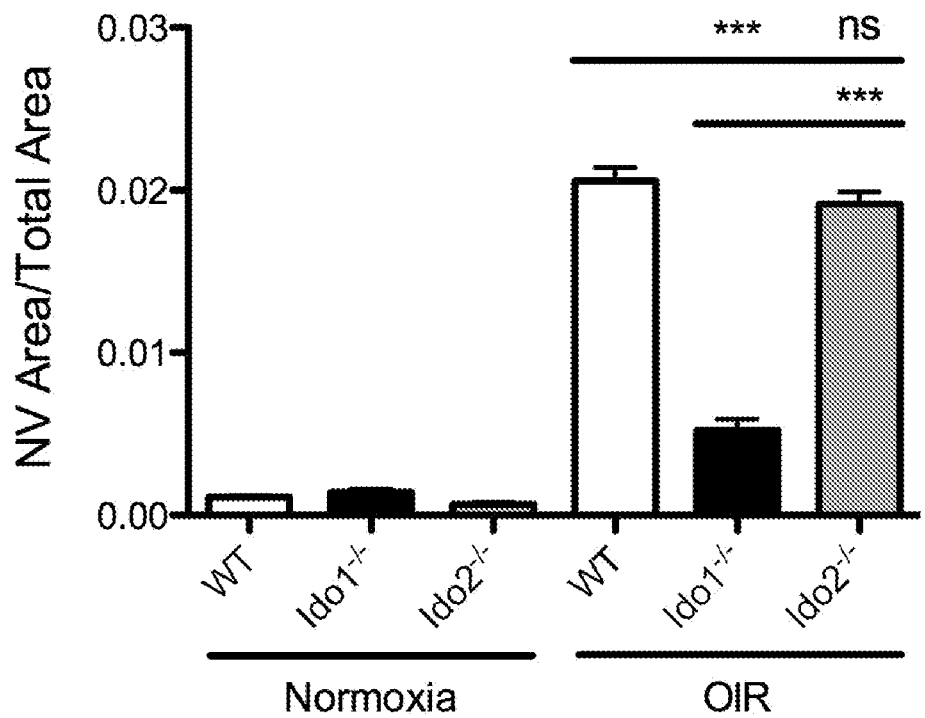
FIG. 4A provides a graph of neovascular (NV) area over total retinal area quantitatively assessed for isolectin stained retinal flat mounts prepared at P17 from WT, Ido1 knockout (Ido1$^{-/-}$), and Ido2 knockout (Ido2$^{-/-}$) neonates exposed to hyperoxia from P7-P12 to induce OIR (N≥16). Corresponding cohorts maintained under constant normoxia were evaluated as a baseline comparison (N≥10). Data are means+/−SEM; *P<0.001; ns, not significant.

B4-Alexa Fluor® 488-isolectin stained retinal flat mounts were prepared at P17 from wild type (WT), Ido1 knockout (Ido1$^{-/-}$), and Ido2 knockout (Ido2$^{-/-}$) neonates exposed to normoxia or to hyperoxia from P7-P12 to induce oxygen-induced retinopathy (OIR). FIG. 3 provides representative microscopic images of B4-Alexa Fluor® 488-isolectin stained retinal flat mounts from WT and Ido1$^{-/-}$ mice at P17 (Ido2$^{-/-}$ images not shown). The left column provides images of retinal flat mounts of mice maintained under normoxia conditions (N≥10). Both WT and Ido1$^{-/-}$ mice show normal vasculature. The middle column and right column (higher magnification) provide images of retinal flat mounts of mice exposed to hyperoxia conditions from P7-P12 to trigger OIR (N≥16). The difference in neovascular tufts between WT and Ido1$^{-/-}$ mice is evident as the Ido1$^{-/-}$ mice show significantly less neovascularization. Neovascular (NV) area over total retinal area was quantitatively assessed for each cohort and the data are presented as a bar graph of the means±SEM in FIG. 4A. Significance was determined between the different pairwise combinations by one-way ANOVA with Tukey's multiple comparison test (***, P<0.001; ns, not significant). As seen in FIG. 4A, neovasculature was only negatively impacted in Ido1$^{-/-}$ mice, but not Ido2$^{-/-}$ mice.

Figure 4B:
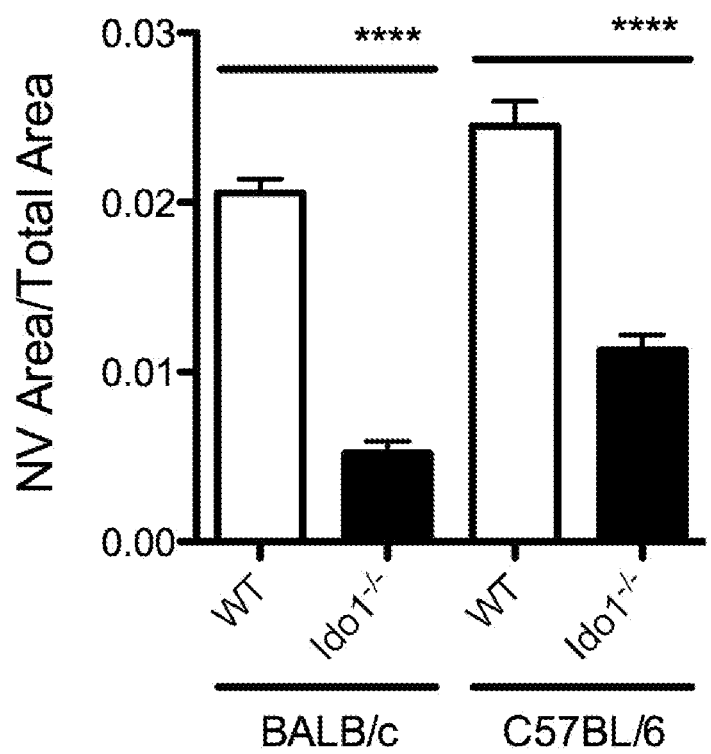
FIG. 4B provides a graph of NV area over total retinal area quantitatively assessed for isolectin stained retinal flat mounts prepared at P17 from WT and Ido1$^{-/-}$ neonates of BALB/c or C57BL/6 strain background exposed to hyperoxia from P7-P12 to induce OIR (N≥14). Data are means+/−SEM; **P<0.0001.

The attenuated OIR neovascularization associated with IDO1 loss was determined to be independent of the strain of mouse. Briefly, B4-Alexa Fluor® 488-isolectin stained retinal flat mounts were prepared at P17 from WT and Ido1$^{-/-}$ neonates of both the BALB/c and C57BL/6 strain backgrounds that were exposed to hyperoxia from P7-P12 to induce OIR (N≥14). NV area over total retinal area was quantitatively assessed for each cohort and the data are presented as a bar graph of the means±SEM in FIG. 4B. Significance between the indicated pairs was determined by 2-tailed Student's t test (****P<0.0001). Similar levels of attenuation in neovascularization are observed in both strains of mice.

Figure 5A:
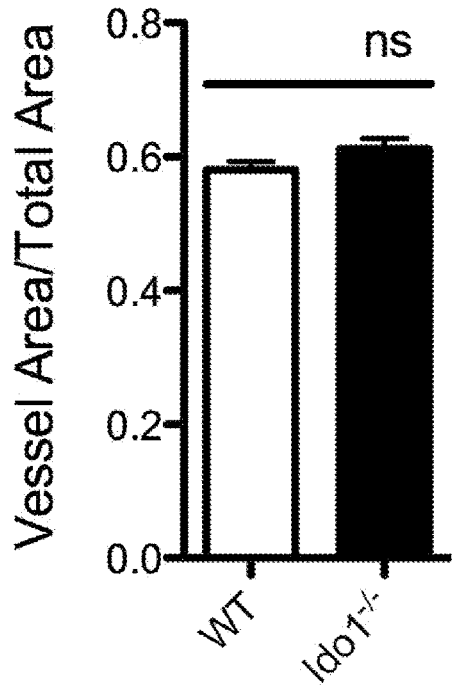
FIG. 5A provides a graph of vessel area over total retinal area quantitatively assessed for isolectin stained retinal flat mounts prepared at P17 from WT and Ido1$^{-/-}$ neonates maintained under constant normoxia (N=10). Data are means+/−SEM; ns, not significant.

Normal vascularization of the retina under normoxic conditions is unaffected by the loss of IDO1. B4-Alexa Fluor® 488-isolectin stained retinal flat mounts were prepared at P17 from WT and Ido1$^{-/-}$ neonates maintained under constant normoxia (N=10). Vessel area over total retinal area was quantitatively assessed for each cohort and the data are presented as a bar graph of the means±SEM in FIG. 5A. Significance between the pair was determined by 2-tailed Student's t test (ns, not significant).

Figure 5B:
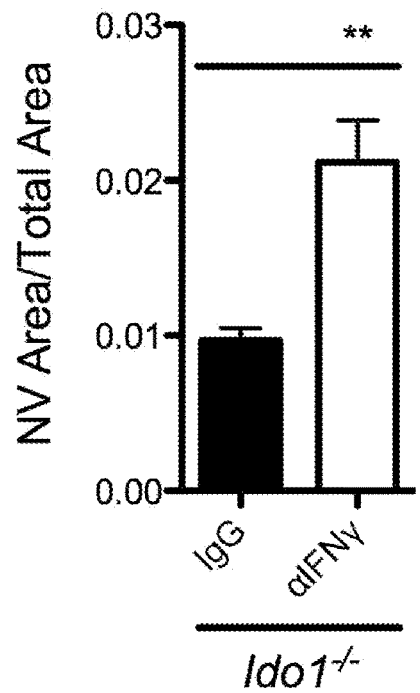
FIG. 5B provides a graph of NV area over total retinal area quantitatively assessed for isolectin stained retinal flat mounts prepared at P17 from WT and Ido1$^{-/-}$ neonates exposed to hyperoxia from P7-P12 to induce OIR followed by intraocular injections of interferon-γ (IFNγ) neutralizing antibody or an isotype matched negative control antibody (N≥9). Data are means+/−SEM; P<0.01.

As noted in Example 1, the concurrent elimination of interferon-γ (IFNγ) in double knockout Ifng$^{-/-}$ Ido1$^{-/-}$ mice reverted the level of neovascularization in the OIR model back to wild type levels. This is consistent with the model that IDO1 supports neovascularization primarily by counteracting the angiostatic activity of IFNγ. Here, it is shown that antibody-mediated IFNγ neutralization restores OIR neovascularization in mice lacking IDO1. B4-Alexa Fluor® 488-isolectin stained retinal flat mounts were prepared at P17 from Ido1$^{-/-}$ neonates exposed to hyperoxia from P7-P12 to induce OIR followed by intraocular injections of IFNγ neutralizing antibody or an isotype matched negative control antibody (N≥9). NV area over total retinal area was quantitatively assessed for each cohort and the data are presented as a bar graph of the means±SEM in FIG. 5B. Significance between the indicated pair was determined by 2-tailed Student's t test (**, P<0.01).

Figure 5C:
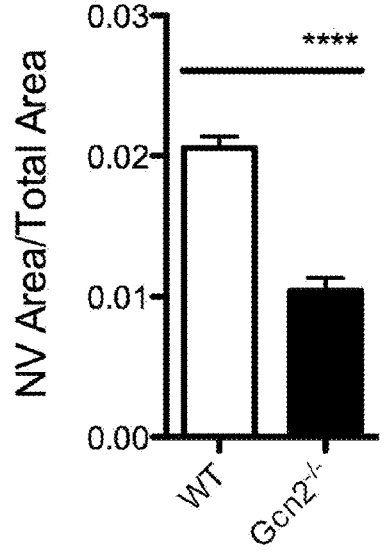
FIG. 5C provides a graph of NV area over total retinal area quantitatively assessed for isolectin stained retinal flat mounts prepared at P17 from WT and Gcn2 knockout (Gcn2$^{-/-}$) neonates exposed to hyperoxia from P7-P12 to induce OIR (N≥12). Data are means+/−SEM; P<0.0001.

GCN2 is part of the IDO1 downstream signaling pathway. Herein, it is shown that the loss of GCN2 (through use of a GCN2 knockout mouse) results in attenuated OIR neovascularization. B4-Alexa Fluor® 488-isolectin stained retinal flat mounts were prepared at P17 from WT and Gcn2$^{-/-}$ neonates exposed to hyperoxia from P7-P12 to induce OIR (N≥12). NV area over total retinal area was quantitatively assessed for each cohort, and the data are presented as a bar graph of the means±SEM in FIG. 5C. Significance between the pair was determined by 2-tailed Student's t test (****, P<0.0001). These results demonstrate that removing a member of the IDO1 downstream signaling pathway produces a similar effect as the loss of IDO1 itself. As such, it is clear that inhibitors of members of the IDO1 downstream pathway may be used to achieve the same effect as IDO1 inhibitors.

Figure 5D:
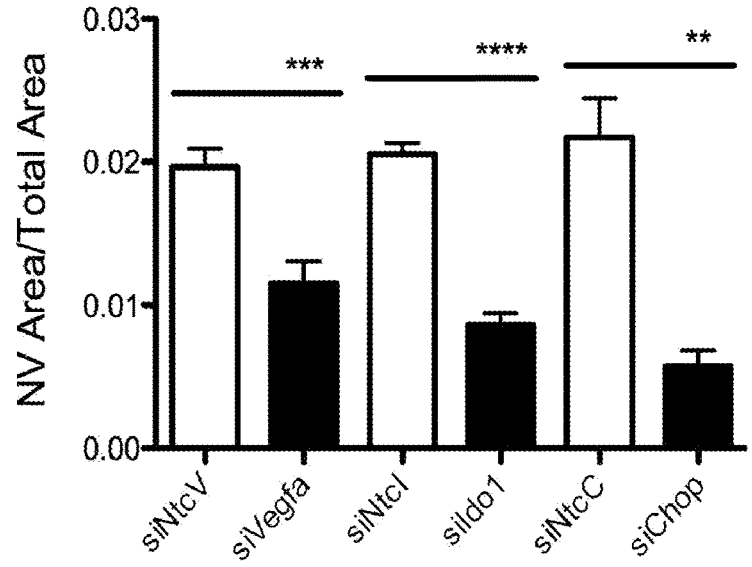
FIG. 5D provides a graph of NV area over total retinal area quantitatively assessed for isolectin stained retinal flat mounts prepared at P17 from WT neonates exposed to hyperoxia from P7-P12 to induce OIR followed by intraocular injections of the indicated siRNAs targeting VEGF-A, Ido1, CHOP, or the corresponding non-target control (siNtc). Data are means+/−SEM; , P<0.0001; *, P<0.001; **, P<0.01.

OIR neovascularization was also attenuated by siRNA mediated knock-down of vascular endothelial growth factor A (VEGF-A), Ido1, and C/EBP homologous protein 10 (CHOP-10; also known as gadd153; herein referred to as CHOP), which is an IDO1 downstream signaling gene. B4-Alexa Fluor® 488-isolectin stained retinal flat mounts were prepared at P17 from WT neonates exposed to hyperoxia from P7-P12 to induce OIR followed by intraocular injections of an siRNA targeting VEGF-A, Ido1, CHOP, or a corresponding non-target control (Ntc). NV area over total retinal area was quantitatively assessed for each cohort, and the data are presented as a bar graph of the means±SEM in FIG. 5D. Significance between the indicated pairs was determined by 2-tailed Student t test (**, P<0.0001; *, P<0.001; **, P<0.01). The reduction in IDO1 was confirmed with anti-IDO1 antibody staining of retinal flat mounts. The use of siRNA demonstrates that administration into the eye of an agent that targets IDO1 also attenuate neovascularization, as observed with the genetic knockouts. The observed effect is at least as robust if not better than targeting VEGF-A. Targeting CHOP demonstrates that removing another component of the IDO1 downstream signaling pathway produces a similar effect as the direct loss of IDO1.

Several publications and patent documents are cited in the foregoing specification in order to more fully describe the state of the art to which this invention pertains. The disclosure of each of these citations is incorporated by reference herein.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method for treating an ocular disease in a subject in need thereof, said method consisting of administering at least one inhibitor of indoleamine 2,3 dioxygenase-1 (IDO1) to the eye of said subject,
wherein said ocular disease is characterized by abnormal vascularization, and
wherein said IDO1 inhibitor is selected from the group consisting of 1-methyl-tryptophan, epacadosat, and GDC-0919.

2. The method of claim 1, wherein said IDO1 inhibitor is 1-methyl-trypophan.

3. The method of claim 1, wherein said ocular disease is characterized by abnormal neovascularization.

4. The method of claim 1, wherein said ocular disease is a retinopathy.

5. The method of claim 1, wherein said ocular disease is retinopathy of prematurity.

6. The method of claim 1, wherein said ocular disease is wet macular degeneration.

7. The method of claim 1, wherein said IDO1 inhibitor is administered topically to the eye.

8. The method of claim 1, wherein said IDO1 inhibitor is administered by intravitreal injection.

9. The method of claim 1, wherein said IDO1 inhibitor is epacadosat.

* * * * *

UNITED STATES PATENT AND TRADEMARK OFFICE
CERTIFICATE OF CORRECTION

| | |
|---|---|
| PATENT NO. | : 10,525,035 B2 |
| APPLICATION NO. | : 15/533201 |
| DATED | : January 7, 2020 |
| INVENTOR(S) | : Alexander J. Muller et al. |

It is certified that error appears in the above-identified patent and that said Letters Patent is hereby corrected as shown below:

In the Claims

In Claim 1, Line 8, replace -- epacadosat -- with -- epacadostat --.

In Claim 9, Line 2, replace -- epacadosat -- with -- epacadostat --.

Signed and Sealed this
Tenth Day of September, 2024

*Katherine Kelly Vidal*

Katherine Kelly Vidal
*Director of the United States Patent and Trademark Office*